United States Patent
Stockdale et al.

(10) Patent No.: US 9,745,449 B2
(45) Date of Patent: Aug. 29, 2017

(54) PHOSPHORUS CONTAINING FLAME RETARDANTS

(71) Applicant: CHEMTURA CORPORATION, Middlebury, CT (US)

(72) Inventors: Zachary D. Stockdale, West Lafayette, IN (US); Mark V. Hanson, West Lafayette, IN (US); Larry D. Timberlake, West Lafayette, IN (US); Subramaniam Narayan, West Lafayette, IN (US); William R. Fielding, West Lafayette, IN (US)

(73) Assignee: LANXESS Solutions US Inc., Middlebury, CT (US)

( * ) Notice: Subject to any disclaimer, the term of this patent is extended or adjusted under 35 U.S.C. 154(b) by 136 days.

(21) Appl. No.: 14/337,500

(22) Filed: Jul. 22, 2014

(65) Prior Publication Data

US 2015/0031805 A1    Jan. 29, 2015

Related U.S. Application Data

(60) Provisional application No. 61/857,741, filed on Jul. 24, 2013.

(51) Int. Cl.
| | |
|---|---|
| C08K 5/5397 | (2006.01) |
| C08K 5/5317 | (2006.01) |
| C08K 5/53 | (2006.01) |
| C08K 5/3492 | (2006.01) |
| C08K 3/32 | (2006.01) |
| C07F 9/53 | (2006.01) |
| C07F 9/6571 | (2006.01) |

(Continued)

(52) U.S. Cl.
CPC .......... *C08K 5/5397* (2013.01); *C07F 9/3808* (2013.01); *C07F 9/3839* (2013.01); *C07F 9/40* (2013.01); *C07F 9/5329* (2013.01); *C07F 9/5333* (2013.01); *C07F 9/657172* (2013.01); *C08K 3/32* (2013.01); *C08K 5/005* (2013.01); *C08K 5/0066* (2013.01); *C08K 5/3492* (2013.01); *C08K 5/34928* (2013.01); *C08K 5/53* (2013.01); *C08K 5/5317* (2013.01); *C08K 5/5333* (2013.01)

(58) Field of Classification Search
CPC ............................... C08K 3/32; C08K 5/5313
See application file for complete search history.

(56) References Cited

U.S. PATENT DOCUMENTS

| 3,689,602 A | 9/1972 | Ismail |
| 3,894,986 A * | 7/1975 | Racky .................. C08K 5/5317 |
| | | 524/123 |

(Continued)

FOREIGN PATENT DOCUMENTS

| DE | 3833977 A1 | 4/1990 |
| EP | 0 245 207 A2 | 11/1987 |

(Continued)

*Primary Examiner* — Lanee Reuther
(74) *Attorney, Agent, or Firm* — Dilworth IP LLC

(57) ABSTRACT

Certain phosphonic acid salts heated at temperatures over 200° C. generate thermally stable, highly efficient flame retardant materials well suited for use as flame retardant additives in polymers. The flame retardants of the invention can be used as the sole flame retardant in a composition or in combination with other flame retardants, synergists or adjuvants.

28 Claims, 2 Drawing Sheets

(51) Int. Cl.
    *C07F 9/38*       (2006.01)
    *C07F 9/40*       (2006.01)
    *C08K 5/00*       (2006.01)
    *C08K 5/5333*     (2006.01)

(56) References Cited

U.S. PATENT DOCUMENTS

| | | |
|---|---|---|
| 4,972,011 A | 11/1990 | Richardson et al. |
| 5,053,148 A * | 10/1991 | von Bonin .............. C04B 38/00 106/122 |
| 5,780,534 A | 7/1998 | Kleiner et al. |
| 6,013,707 A | 1/2000 | Kleiner et al. |
| 6,255,371 B1 | 7/2001 | Schlosser et al. |
| 6,365,071 B1 | 4/2002 | Jenewein et al. |
| 6,472,448 B2 | 10/2002 | Witte et al. |
| 6,547,992 B1 | 4/2003 | Schlosser et al. |
| 7,531,585 B2 | 5/2009 | Ozawa et al. |
| 8,445,718 B2 | 5/2013 | Suwa et al. |
| 2006/0138391 A1 * | 6/2006 | Drewes .............. C08K 5/34928 252/601 |
| 2007/0029532 A1 | 2/2007 | Hansel et al. |

FOREIGN PATENT DOCUMENTS

| | | |
|---|---|---|
| EP | 0 393 421 A2 | 10/1990 |
| WO | 2005097894 A1 | 10/2005 |
| WO | 2010131678 A1 | 11/2010 |
| WO | WO 2012/045414 A1 | 4/2012 |
| WO | WO 2012/088080 A1 | 6/2012 |

* cited by examiner

PHOSPHORUS CONTAINING FLAME RETARDANTS

This application claims benefit under 35 USC 119(e) of U.S. Provisional Application No. 61/857,741 filed Jul. 24, 2013, the disclosure of which is incorporated herein by reference.

BACKGROUND OF THE INVENTION

Polymers, such as polyolefins, polyesters, polycarbonates, polyamides, polyurethanes, epoxy resins, and other thermoplastic or thermoset polymer resins, are frequently made more flame retardant by incorporating therein a phosphorus-containing compound, a halogen-containing compound or a mixture thereof. U.S. Pat. No. 3,689,602, for example, discloses halogenated phosphoric acid esters as flame-retardant additives for plastics.

Some polymers are processed at high temperatures, for example 200° C., 220° C., 250° C. or higher, and many known flame retardants are not suitable under these conditions because they are too volatile, not sufficiently thermally stable, have an adverse effect on processing, etc. Certain organophosphorus flame retardant compounds, such as some phosphate esters, can also exhibit a plasticizing effect which may adversely affect mechanical properties of the polymers into which they are added. In addition, compounds such as some phosphates are relatively unstable to hydrolysis, which can result in undesired formation of various phosphoric acid compounds.

Salts of phosphorus containing acids are known flame-retardant additives, in particular for thermoplastic polymers. U.S. Pat. No. 3,894,986 discloses flame retardant thermoplastic polyesters containing alkali salts of phosphonic acids, e.g., the mono sodium salt of ethane-phosphonic acid or a sodium salt of a mono-methyl ester of an alkane-phosphonic acid. U.S. Pat. No. 4,972,011 discloses aluminum salts of alkylphosphonic acids or mono-alkyl esters of alkane-phosphonic acids, i.e., salts of compounds of formula (Ia), wherein R is for example methyl, ethyl, propyl or isopropyl etc., unsubstituted or substituted by one or more halo or hydroxy groups; and R' is hydrogen, methyl, ethyl, propyl, or isopropyl.

(Ia)

DE 3833977 discloses metal salts of compounds of formula (Ia) prepared from reactions of dimethylmethylphosphinate and metal oxides or hydroxides in water at high pressures and temperatures from 120 to 200° C.; reactions run in aqueous solution under elevated pressures at temperatures up to 190° C. in an autoclave are exemplified. Adducts of these salts with amines such as ethylene diamine and melamine, and use of the adducts as flame retardants in thermoplastics are also disclosed.

Salts of phosphinic acids, i.e., compounds of formula (II) wherein $R_1$ and $R_2$ are alkyl or carbon based aromatic, are also known flame-retardant additives for thermoplastic polymers.

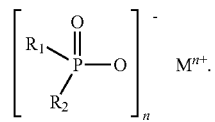

(II)

Salts wherein M is selected from Mg, Ca, Al, Sb, Sn, Ge, Ti, Zn, Fe, Zr, Ce, Bi, Li, Na, K or protonated nitrogen base are known. For example, U.S. Pat. Nos. 5,780,534 and 6,013,707 disclose that calcium phosphinates and aluminum phosphinates of Formula (II) are particularly effective in polyester, for example, calcium and aluminum salts of dimethylphosphinic acid, ethylmethylphosphinic acid, diethylphosphinic acid, n-propylmethylphosphinic acid, n-propylethylphosphinic acid, di-n-propylphosphinic acid, diisopropylphosphinic acid or diphenylphosphinic acid.

As is common with many flame retardant systems, the performance of phosphorus containing acid derivatives can be enhanced by the presence of other flame retardant agents, synergists and adjuvants. U.S. Pat. No. 6,472,448 discloses flame retardant rigid polyurethane foam wherein a combination of oxalkylated alkylphosphonic acids and ammonium polyphosphate is present as flame retardant.

U.S. Pat. No. 6,365,071 discloses a synergistic flame retardant combination for thermoplastic polymers, e.g., engineering plastics, especially for polyesters, comprising A) a phosphinic salt of the formula (II) above, e.g., aluminum dimethylphosphinate, aluminum methylethylphosphinate, and aluminum methylpropylphosphinate and B) a nitrogen compound such as allantoin, i.e., (2,5-dioxo-4-imidazolidinyl)urea, benzoguanamine, glycoluril, i.e., tetrahydroimidazo[4,5-d]imidazole-2,5-dione, urea cyanurate, melamine cyanurate and melamine phosphate.

U.S. Pat. No. 6,255,371 discloses a flame retardant combination comprising, A) a phosphinate of formula (II) above, e.g., a diethyl phosphinate where M is calcium, magnesium, aluminum and/or zinc, and B) condensation or reaction products of melamine e.g., melamine polyphosphate, melam polyphosphate and melem polyphosphate.

U.S. Pat. No. 6,547,992 discloses a flame retardant combination for thermoplastic polymers comprising phosphinates and small amounts of inorganic and/or mineral compounds which do not contain nitrogen. WO 2012/045414 discloses a flame retardant composition comprising A) a phosphinic salt of the formula (II) above wherein M is selected from Mg, Ca, Al, Sb, Sn, Ge, Ti, Zn, Fe, Zr, Ce, Bi, Li, Na, K or a protonated nitrogen base; B) a metal salt of phosphorous acid; and other optional components.

The phosphinates cited above, e.g., U.S. Pat. Nos. 6,365,071 and 6,255,371, are said to be thermally stable, and neither decompose the polymers during processing nor affect the process of preparing the plastic composition. The phosphinates are not volatile under the customary conditions of preparation and processing of thermoplastic polymers. However, these materials are not necessarily suitable for use in all polymer systems and may create problems for processing or may lack the flame retardant effectiveness needed for certain polymers. There is still a need for flame retardants with greater efficiency at lower additive concentrations and improved processability for use in preparing flame retardant polymer compositions with highly desirable physical properties.

Phosphonic acid salts, i.e., salts metal salts of compounds according to formula (Ia), are also reported to be thermally stable, but this is of course a relative term. As disclosed in US 2007/0029532, decomposition of such phosphonic acid salts is well known at temperatures encountered during processing of polyesters and polyamides, damaging the polymers in the process.

U.S. Pat. No. 5,053,148 discloses heat resistant foams obtained by heating metal phosphonates or metal phosphonate precursors to temperatures of above 200° C. useful, e.g., as electrical and/or heat insulation materials. Also disclosed is the use of this reaction to expand or render porous other substrates. Such substrates include, for example, thermoplastic polymers or plastics such as aromatic polyesters, polyethers, polysulfides, polyamides, polycarbonates, polyimides, polysiloxanes or polyphosphazenes, can be introduced into the foaming operation as a mixture with metal phosphonates and/or their precursors.

While U.S. Pat. No. 5,053,148 may suggest that a porous polyamide may be produced by heating a mixture of a metal phosphonate and a polyamide according to the "foaming process", nothing in U.S. Pat. No. 5,053,148 addresses or refutes the disclosure of US 2007/0029532 that decomposition of such phosphonic acid salts at high temperature gives "brittle compositions which are unusable" as an engineering thermoplastic. Outside of suggesting that a porous foam may be produced by heating metal phosphonate and a polymer such as polyamide, U.S. Pat. No. 5,053,148 contains no mention of what the properties of such an unexemplified material might be.

The difficulty of thermally processing certain thermoplastic resins in the presence of alkylphosphonic acid metal salts, and the poor physical properties of the polymer composition obtained thereby, has been confirmed by experimentation. However, it has now been found that the products obtained by heating certain alkylphosphonic acid metal salts, such as aluminum salts, calcium salts, zinc salts etc., at temperatures in excess of 200° C. are thermally stable at temperatures above 400° C. and can be thermally incorporated onto thermoplastic polymer resins without adversely impacting the resulting physical properties of the polymer composition obtained. Further, it is found that polymer compositions comprising the flame retardants of the invention, e.g., thermoset or thermoplastic compositions, exhibit excellent flame retardant activity, either alone or in combination with other flame retardants, synergists or adjuvants.

SUMMARY OF THE INVENTION

Compounds of Formula (I)

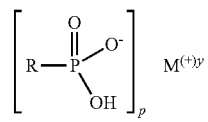

wherein y is a number of from 1 to 7, e.g., from 1 to 4, M is a metal cation with a formal charge of (+)y, p is a number of from 1 to 7, e.g., from 1 to 4, and R is e.g., alkyl, aryl, alkylaryl or arylalkyl, undergo reaction when heated at temperatures over 200° C., e.g., at temperatures of 220° C. to 250° C. or higher, e.g. from about 200° C., 220° C. or 250° C. to about 400° C. to form a different chemical species that is typically thermally stable to temperatures of 400° C. and higher and are well suited for use as flame retardant additives in polymers. These reaction products have improved flame retardant properties and relative to the compounds of formula (I) and are more readily processed into polymer resins, such as polyamides, without negatively impacting the physical property of the resin. The mechanism of action is uncertain at this time, however, excellent and surprising results are obtained when the materials of the invention are used in conjunction with phosphinic acid salts, i.e., compounds of formula (II), and in a manner that suggests the possibility that the two materials may have different and complimentary activity.

This invention provides a flame retardant comprising the product obtained by the thermal treatment of compounds of formula (I), a process for preparing the flame retardant, synergistic blends of the flame retardant with other flame retardants or flame retardant synergists e.g., blends of the flame retardant of the invention with phosphinic acid salts, and polymer compositions comprising the inventive flame retardant or synergistic blends.

Also provided is a method for preparing flame retardant polymers, which method comprises heating compounds of formula (I) under conditions that chemically transform said compounds to the thermally stable flame retardant material of the invention as described above, and then incorporating the thus prepared thermally stable flame retardant into a polymer resin, e.g., by melt processing of the polymer and flame retardants at elevated temperature. A particular embodiment provides a method wherein the thermally stable flame retardant prepared by heating compounds of formula (I) is added to a polymer resin along with phosphinic acid salts formula (II) and/or other synergists.

DESCRIPTION OF THE INVENTION

Figure 1:
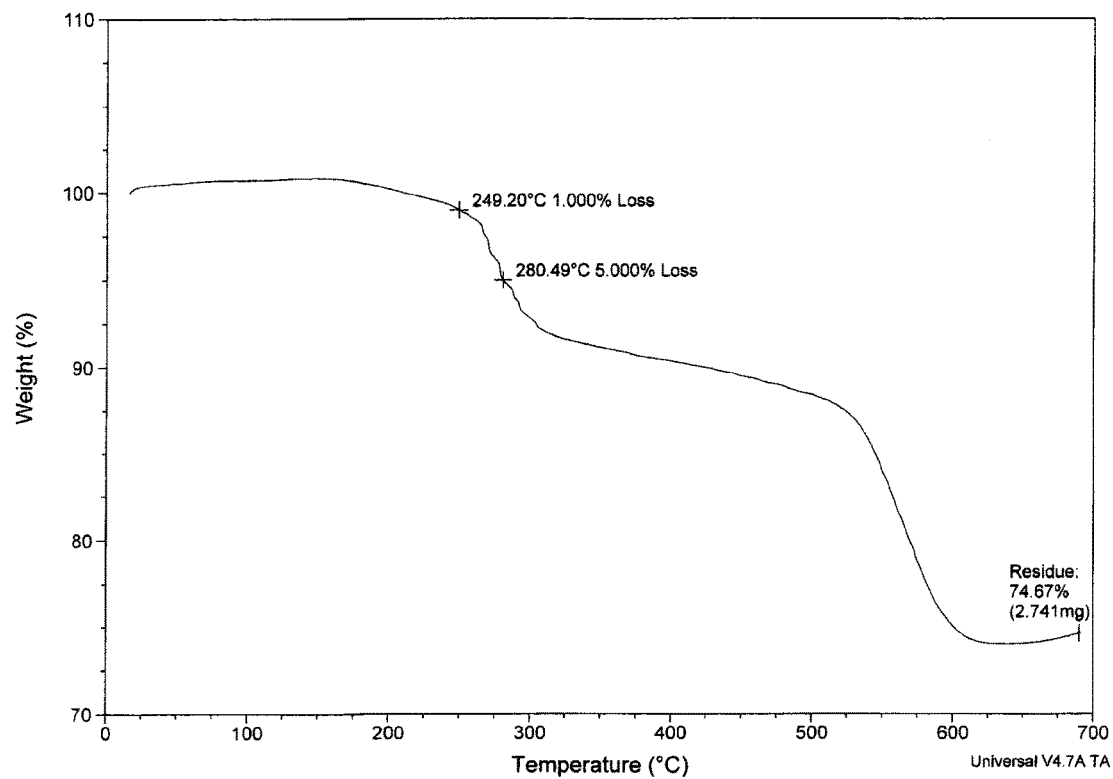
FIG. 1 displays the thermal analysis data of tris-[methylphosphonic acid] aluminum salt, prepared according to Comparative Example 1, which is the starting material for the flame retardant material of Example 1.

One embodiment of the invention is a flame retardant polymer composition comprising:
a) a thermoset or thermoplastic polymer, e.g., a thermoplastic polymer,
b) from 1% to 50%, by weight based on the total weight of the flame retardant composition of a flame retardant material obtained by heating one, or more than one, phosphonic acid salt, i.e., compounds of formula (I)

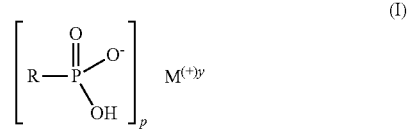

wherein R is an alkyl, aryl, alkylaryl or arylalkyl group, p is a number of from 1 to 7, e.g., from 1 to 4, e.g., 1, 2, 3 or 4, M is a metal, y is a number of from 1 to 7, e.g., from 1 to 4, e.g., 1, 2, 3 or 4, often 2 or 3, so that $M^{(+)y}$ is a metal cation where (+)y represents the charge formally assigned to the cation,
at temperatures of 200° C. or higher, e.g., 220° C. or higher, generally at temperatures of 250° C. or higher, e.g. from about 250° C. to about 400° C. or from about 260° C. to about 360° C., and c) optional additional flame retardants or flame retardant synergists.

For example, in formula (I), $M^{(+)y}$ where y is 1 represents a mono-cation such as $Li^+$, $Na^+$ or $K^+$, $M^{(+)y}$ where y is 2 represents a di-cation such as $Mg^{++}$, $Ca^{++}$ or $Zn^{++}$ and the like, $M^{(+)y}$ where y is 3 represents a tri-cation such as $Al^{+++}$, etc. As is common with organometallic species, the formulae are idealized and the starting materials may include complex salts or salts where certain atomic valences are shared such as where a single oxygen anion is shared between two metal cations, etc. Typically, the starting salt is charged balanced, that is, a compound of formula (I) wherein p=y, e.g., when $M^{(+)y}$ is $Na^+$, p is 1, when M is $Al^{+++}$ p is 3, etc.

While not wanting to be bound by theory, spectroscopic data and other analysis suggest that thermal treatment of a compound of formula (I) within the temperature treatment range of the invention generates a material comprising a compound that is believed to be generically represented by the empirical formula (IV) and complex dehydration products thereof:

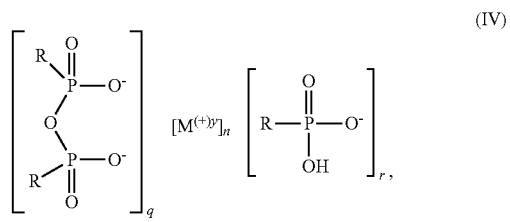

wherein R and M are as defined for formula (I), q is a number of from 1 to 7, e.g., 1, 2 or 3, r is a number from 0 to 5, e.g., 0, 1 or 2, often 0 or 1, y is a number of from 1 to 7, e.g., from 1 to 4, and n is 1 or 2, provided that 2(q)+r=n(y). Typically, thermal treatment of a compound of formula (I) according to the invention generates a material comprising more than one compound, at least one of which is believed to be generically represented by the empirical formula (IV) and complex dehydration products thereof. As is common with organometallic species, the formula (IV) is idealized and the product may include polymeric salts, complex salts, salts where certain atomic valences are shared, etc.

For example, when M is aluminum, i.e., when a compound of formula (I) wherein M is Al is heated according to the invention, elemental analysis suggests the formation of a product having an empirical formula (IV) wherein q is 1, r is 1, n is 1 and y is 3.

The flame retardant material obtained according to the invention is more thermally stable and exhibits greater flame retardant activity and has improved processability in a variety of polymer resins than the starting phosphonic acid salts of formula (I).

The polymer of flame retardant composition of the present invention may be any polymer known in the art, such as polyolefin homopolymers and copolymers, rubbers, polyesters, epoxy resins, polyurethanes, polyalkylene terephthalates, polysulfones, polyimides, polyphenylene ethers, styrenic polymers and copolymers, polycarbonates, acrylic polymers, polyamides, polyacetals, epoxy resins and biodegradable polymers. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or made by means well known in the art.

The flame retardant of the invention is particularly useful in thermoplastic polymers that are processed and/or used at high temperatures, for example, styrenic polymers including HIPS, polyolefins, polyesters, polycarbonates, polyamides, polyurethanes, polyphenylene ethers and the like.

For example, the polymer may be a polyester-series resin, a styrenic resin, a polyamide-series resin, a polycarbonate-series resin, a polyphenylene oxide-series resin, a vinyl-series resin, an olefinic resin, an acrylic resin, epoxy resin, or a polyurethane. The polymer can be a thermoplastic or a thermoset resin and may be reinforced, e.g., glass reinforced. More than one polymer resin may be present. In particular embodiments the polymer is an engineering polymer, e.g., a thermoplastic or reinforced thermoplastic polymer, e.g., glass reinforced thermoplastic polymer, such as an optionally glass filled polyester, epoxy resin or polyamide, for example, a glass-filled polyester such as a glass filled polyalkylene terephthalate, or a glass filled polyamide.

Polyester-series resins include homopolyesters and copolyesters obtained by, for example, polycondensation of a dicarboxylic acid component and a diol component, and polycondensation of a hydroxycarboxylic acid or a lactone component, for example, aromatic saturated polyester-series resin, such as polybutylene terephthalate or polyethylene terephthalate.

Polyamide-series resins include polyamides derived from a diamine and a dicarboxylic acid; polyamides obtained from an aminocarboxylic acid, if necessary in combination with a diamine and/or a dicarboxylic acid; and polyamides derived from a lactam, if necessary in combination with a diamine and/or a dicarboxylic acid. The polyamide also includes a copolyamide derived from at least two different kinds of polyamide constituent components. Examples of polyamide-series resins include aliphatic polyamides such as nylon 46, nylon 6, nylon 66, nylon 610, nylon 612, nylon 11 and nylon 12, polyamides obtained from an aromatic dicarboxylic acid, e.g., terephthalic acid and/or isophthalic acid, and an aliphatic diamine, e.g., hexamethylenediamine or nonamethylenediamine, and polyamides obtained from both aromatic and aliphatic dicarboxylic acids, e.g., both terephthalic acid and adipic acid, and an aliphatic diamine, e.g., hexamethylenediamine, and others. These polyamides may be used singly or in combination.

In one embodiment of the invention, the polymer comprises a polyamide typically processed at high temperatures, e.g., 300° C. or higher, in some embodiments 320° C. or higher, e.g. 340° C. or higher. Examples of high temperature polyamides include thermoplastic resins such as nylon 46, nylon 4T, nylon 6T/66 copolymers, nylon 9T and the like.

The flame retardant (b) exhibits excellent activity in polymer systems either as the sole flame retardant or in combination with other flame retardants, synergists or adjuvants. The concentration of the inventive flame retardant in the polymer composition is of course dependent on the exact chemical composition of the flame retardant, the polymer and other components found in the final polymer composition. For example, when used as the sole flame retarding component of a polymer formulation the inventive flame retardant may be present in a concentration of from about 1 to about 50%, e.g., 1 to 30%, by weight of the total weight of the final composition. Typically, when used as the sole flame retardant there will be at least 2% of the inventive material present, for example 3% or more, 5% or more, 10% or more, 15% or more, 20% or more or 25% or more. In many embodiments, the inventive flame retardant is present in amounts up to 45%, while in other embodiments, the amount of inventive flame retardant is 40% of the polymer composition or less, e.g., 35% or less. Obviously, when used in combination with other flame retardants or flame retardant synergists, less of the inventive material should be needed.

Any known compounding techniques may be used to prepare the flame retardant polymer composition of the invention, for example, the flame retardant may be introduced into molten polymer by blending, extrusion, fiber or film formation etc. In some cases the flame retardant is introduced into the polymer at the time of polymer formation or curing, for example, the flame retardant of the invention may be added to a polyurethane prepolymer prior to crosslinking or it may be added to a polyamine or alkyl-polycarboxyl compound prior to polyamide formation or to an epoxy mixture prior to cure.

Other embodiments of the invention are to the flame retardant material and synergistic blends of the flame retardant material and other components. The flame retardant of the invention is obtained by heating one, or more than one, phosphonic acid salt, i.e., compounds of formula (I)

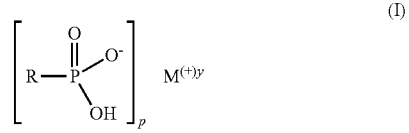

(I)

wherein R is an alkyl, aryl, alkylaryl or arylalkyl group, p is a number of from 1 to 7, e.g., 1 to 4, e.g., 1, 2, 3 or 4, M is a metal, y is a number of from 1 to 7, e.g., 1 to 4, e.g., 1, 2, 3 or 4, so that $M^{(+)y}$ is a metal cation where (+)y represents the charge formally assigned to the cation, at temperatures of 200° C. or higher, e.g., 220° C. or higher, generally at temperatures of 250° C. or higher, e.g. from about 250° C. to about 400° C. or from about 260° C. to about 360° C. As stated above, the material generated by heating compounds of formula (I) at the listed temperature is believed to be compound or a mixture of compounds one or more of which is believed to be generically represented by the empirical formula (IV):

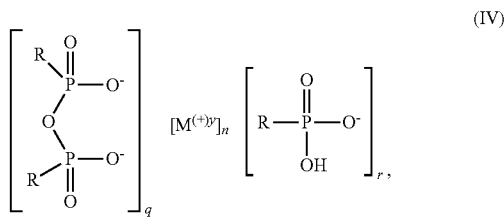

(IV)

wherein R and M are as defined for formula (I), q is a number of from 1 to 7, e.g., 1, 2 or 3, r is a number from 0 to 5, e.g., 0, 1 or 2, often 0 or 1, y is a number of from 1 to 7, e.g., from 1 to 4, e.g., 1, 2, 3, or 4, and n is 1 or 2, provided that $2(q)+r=n(y)$.

The phosphonic acid salts of formula (I) are known and various methods for their preparation are described in the art. For example, US 2006/0138391 discloses compounds of formula (I) wherein R is hydrogen, $C_{1-18}$ alkyl, $C_{5-6}$ cycloalkyl, $C_{2-6}$ alkenyl, $C_{6-10}$ aryl, or $C_{7-11}$ aralkyl, which alkyl, alkenyl, aryl, or aralkyl can be unsubstituted or substituted by halogen, hydroxyl, amino, $C_{1-4}$ alkylamino, di-$C_{1-4}$ alkylamino, $C_{1-4}$ alkoxy, carboxy or $C_{2-5}$ alkoxycarbonyl; and M can be selected from, e.g., Group IA, IB, IIA, IIB, IIIA, IVA, VA or VII of the Periodic Table, for example Li, K, Na, Mg, Ca, Ba, Zn, Ge, B, Al, Cu, Fe, Sn or Sb, etc. It is noted that in US 2006/0138391 none of the compounds corresponding to the formula (I) above were heated above 200° C. or compounded into a polymer resin at elevated temperature. The only salt actually exemplified in US 2006/0138391 was the aluminum salt of methyl methylphosphonic acid, i.e., the salt of a compound of formula (Ia) above wherein R and R' are methyl, i.e.:

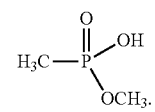

The starting material for the flame retardant of the present invention, i.e., compound of formula (I), can be conveniently selected from salts disclosed in US 2006/0138391 and elsewhere in the art. Compounds of formula (I) useful in the invention may also comprise other R groups not found in US 2006/0138391, such as aryl substituted by alkyl, and it is possible that compounds of formula (I) comprising metal cations not specifically mentioned therein could be useful as starting materials.

In some embodiments of the invention, the salts of formula (I) comprise compounds wherein R is $C_{1-12}$ alkyl, $C_{6-10}$ aryl, $C_{7-18}$ alkylaryl, or $C_{7-18}$ arylalkyl group, wherein said groups are further substituted as described in US 2006/0138391, but often R is unsubstituted $C_{1-12}$ alkyl, $C_{6-10}$ aryl, $C_{7-18}$ alkylaryl, or $C_{7-18}$ arylalkyl. For example, R is substituted or unsubstituted, typically unsubstituted, $C_{1-6}$ alkyl, $C_6$ aryl, $C_{7-10}$ alkylaryl, or $C_{7-12}$ arylalkyl, e.g., $C_{1-4}$ alkyl, $C_6$ aryl, $C_{7-19}$ alkylaryl, or $C_{7-10}$ arylalkyl.

While in the most general embodiments of the invention $M^{(+)y}$ may be almost any metal cation, M is generally selected from Li, K, Na, Mg, Ca, Ba, Zn, Zr, Ge, B, Al, Si, Ti, Cu, Fe, Sn or Sb, for example, e.g., Li, K, Na, Mg, Ca, Ba, Zn, Zr, B, Al, Si, Ti, Sn or Sb, in many embodiments M is Li, K, Na, Mg, Ca, Ba, Zn, Zr, B, Al, Sn or Sb, and in certain embodiments M is Al, Zn or Ca. For example, excellent results are achieved when M is Al or Ca.

R as alkyl is a straight or branched chain alkyl group having the specified number of carbons and includes e.g., unbranched alky such as methyl, ethyl, propyl, butyl, pentyl, hexyl heptyl, octyl, nonyl, decyl, undecyl, dodecyl, and unbranched alkyl such as iso propyl, iso-butyl, sec-butyl, t-butyl, ethyl hexyl, t-octyl and the like. For example, R as alkyl is methyl, ethyl, propyl, iso propyl, butyl, iso butyl, sec-buty, t-butyl, often R is methyl, ethyl, propyl or isopropyl, for example methyl.

Typically when R is aryl it is phenyl or naphthyl, for example, phenyl. Examples of R as alkylaryl include phenyl substituted by one or more alkyl groups, for example groups selected from methyl, ethyl, propyl, isopropyl, butyl, iso butyl, sec-buty, t-butyl, and the like. Examples of R as arylalkyl, include for example, benzyl, phenethyl, styryl, cumyl, phenpropyl and the like.

In one embodiment R is methyl, ethyl, propyl, isopropyl, phenyl or benzyl, e.g., methyl or phenyl.

In certain embodiments, for example, the starting material is a compound of formula (I) wherein R is methyl, ethyl, propyl, isopropyl, benzyl or phenyl, M is Al, Zn or Ca, and p is 2 or 3. In one particular embodiment R is methyl, ethyl, propyl, isopropyl, or phenyl, p=3 and M is Al; in another particular embodiment R is methyl, ethyl, propyl, isopropyl, or phenyl, p=2 and M is Zn or Ca, e.g., Ca.

The amount of time it takes to convert the phosphonic acid salts of formula (I) to the flame retardant of the invention will vary depending on a variety of factors, including, e.g., the chemical structure of the starting phosphonic acid salt, temperature of the reaction, other reaction conditions etc. For example, higher temperatures can lead to quicker reaction times. It is believed that water is produced in during the reaction and the presence of a water absorbent or vacuum may also reduce reaction times. Design of the reaction vessel, the presence of other materials during heating, etc., can also impact the time of reaction.

Good conversion is frequently obtained by heating a phosphonic acid salt of formula (I) at temperatures of e.g., at least 200° C., 220° C., 250° C. or higher, for a time of 20 hours or less, typically less than 12 hours. In certain circumstances the time can be extremely short, for example, use of higher temperatures, e.g., 250° C. to 400° C. or temperatures above 400° C., in a reaction vessel or environment that makes heat transfer to the starting material highly efficient can greatly reduce reaction times to, for example, less than 0.2 hour, 0.1 hour, or 0.01 hours or less and complete reactions times measured in seconds or less are possible.

Generally full conversion to the flame retardant of the invention is obtained by heating the starting phosphonic acid salt at temperatures of from about 200° C. to about 400° C. for from about 0.01 or 0.2 to about 20 hours, often about 0.1 or 0.2 to about 12 hours, or from about 1 to about 8 hours, although as stated above the amount of time for full conversion will depend on the temperature. For example, heating the phosphonic acid salt of formula (I) at from about 250° C. to about 400° C. will require less than 12 hours of heating, e.g., from about 1 to 8 hours. Excellent results have been obtained when the starting phosphonic acid salt is heated at from about 260° C. to about 340° C. for about 1 to 6 hours, e.g., for about 2 to about 6 hours.

For example, tris-[methylphosphonic acid] aluminum salt, i.e. a water soluble solid compound of formula (III) wherein R is methyl, is heated at a temperature of from 250 to about 320° C. for about 2 to about 6 hours to form a solid material that is, in contrast to the starting material, not soluble in water and stable at temperatures in excess of 400° C. Higher reaction temperatures can be used, however, as seen in the examples, heating at about 280° C. for 4 hours yields excellent results.

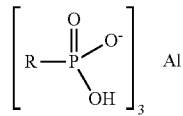

(III)

Likewise, heating tris-[ethylphosphonic acid] aluminum salt, i.e. the compound of formula (III) wherein R is ethyl, or tris-[phenylphosphonic acid] aluminum salt, i.e. the compound of formula (III) wherein R is phenyl, under similar conditions leads to analogous ethyl and phenyl containing flame retardant material.

Generally, the selected phosphonic acid metal salt or mixture of salts used as starting material is heated on its own, i.e., in the absence of other materials. However, one could heat these salts in the presence of e.g., an inert carrier, another flame retardant, or other potential additives, etc., although the presence of added water is typically avoided as it is believed that water is eliminated from the starting material during reaction. For example, the starting materials could be mixed with other flame retarding materials, polymer stabilizers, or other known polymer additives before heating above 200° C. The thermal transformation of the salts could also take place in the presence of a small amount of polymer as an inert carrier, however, one must be careful to avoid a situation wherein the conversion of the starting salt is impeded by the presence of other materials. For example, a polymer or other material may melt under the reaction temperatures and coat the salt, or even react with the salt, producing undesired consequences.

In many embodiments a compound of formula (I) undergoes thermal treatment in the absence of other components. If a polymer or other inert carrier is present during the reaction it is present in an amount that is less than the amount of phosphonic acid metal salt, e.g., less than 50% or less than 25% by weight of the combination of phosphonic acid metal salt and polymer, typically less 10%, for example less than 5% or from 0 to 2% by weight. As the salt of formula (I) is believed to liberate water in the reaction it is advisable to avoid heating the salt above 200° C. in the presence of a material that is unstable in the presence of water at high temperature including polymers capable of undergoing hydrolysis.

According to the present invention, the phosphonic acid metal salt of formula (I) is thermally transformed to a different, more thermally stable flame retardant material before it is incorporated into the bulk of the polymer that it is to protect. Contrary to the salts of formula (I), which are also known as flame retardants, the present flame retardants are stable at processing temperatures above 200° C. and do not undergo reaction which may have a negative impact on, e.g., polymers such as polyesters and polyamides which contain linkages susceptible to reaction and cleavage.

For example, polyalkylene phthalates, polyamides and many other condensation polymers are processed at high temperatures. At high temperatures, salts of formula (I) undergo reactions that apparently liberate water, which could lead to hydrolysis at the ester or amide linkages, causing chain cleavage and loss of molecular weight and desired physical properties. In Comparative Example 1, attempts were made to compound a salt of formula (I) into a glass filled polyamide at elevated temperature resulting in polymer degradation. While it is not known whether the elimination of water during the thermal treatment of the salts of formula (I) was responsible for the observed degradation, flame retardants of the invention from Examples 1, 2 and 3 were successfully incorporated into the same glass filled polyamide without noticeable degradation.

The flame retardant of the invention may be used with a variety of other flame retardants, synergists or flame retardant adjuvants as known in the art. For example, the flame retardant of the invention may be formulated with one or more materials selected from:
carbon black, graphite, carbon nanotubes, silicones; polyphenylene ether (PPE), phosphine oxides and polyphosphine oxides, e.g., benzylic phosphine oxides, poly benzylic phosphine oxides and the like;
melamine, melamine derivatives and condensation products, melamine salts such as, but not limited to, melamine cyanurate, melamine borate, melamine phosphates, melamine metal phosphates, and the like;

inorganic compounds including clays, metal salts such as hydroxides, oxides, oxide hydrates, borates, carbonates, sulfates, phosphates, phosphites, hypophosphites, silicates, mixed metal salts, etc., e.g., talc and other magnesium silicates, calcium silicate, aluminosilicate, aluminosilicate as hollow tubes (DRAGONITE), calcium carbonate, magnesium carbonate, barium sulfate, calcium sulfate, HALLOYSITE or boron phosphate, calcium molybdate, exfoliated vermiculite, zinc stannate, zinc hydroxystannate, zinc sulfide and zinc borate, zinc molybdate (KEMGARD 911A/B), zinc phosphate (KEMGARD 981), magnesium oxide or hydroxide, aluminum oxide, aluminum oxide hydroxide (Boehmite), aluminum trihydrate, silica, tin oxide, antimony oxide (III and V) and oxide hydrate, titanium oxide, and zinc oxide or oxide hydrate, zirconium oxide and/or zirconium hydroxide and the like.

Unless otherwise specified, in the context of the present application, the term "phosphate" when used as a component in a "phosphate salt", such as in metal phosphate, melamine phosphate, melamine metal phosphate, etc., refers to a phosphate, hydrogen phosphate, dihydrogen phosphate, pyrophosphate, polyphosphate, or a phosphoric acid condensation products anion or polyanion.

Likewise, unless otherwise specified, in the context of the present application, the term "phosphite" when used as a component in a "phosphite salt", such as in metal phosphite, etc., refers to a phosphite or hydrogen phosphite.

The flame retardant of the invention may also be formulated with other flame retardants such as halogenated flame retardants, alkyl or aryl phosphine oxide flame retardants, alkyl or aryl phosphate flame retardants, alkyl or aryl phosphonates, alkyl or aryl phosphinates, and salts of alkyl or aryl phosphinic acid. One particular embodiment provides a synergistic mixture of the flame retardant of the invention and a phosphinic salt of formula (II), e.g., an aluminum tris(dialkylphosphinate).

Thus, in many embodiments the flame retardant polymer composition according to the invention comprise the polymer (a), the flame retardant (b), and further comprise (c) one or more additional flame retardants, and/or one or more synergists or flame retardant adjuvants.

For example, in some embodiments the flame retardant polymer composition comprises one or more additional flame retardants, e.g., halogenated flame retardants, phosphine oxide flame retardants, alkyl or aryl phosphonates, or salts of alkyl or aryl phosphinates, e.g., an aluminum tris(dialkylphosphinate) such as aluminum tris(diethylphosphinate).

In some embodiments the flame retardant polymer composition comprises one or more synergists or flame retardant adjuvants, e.g., melamine, melamine derivatives and condensation products, melamine salts, phosphine oxides and polyphosphine oxides, metal salts such as hydroxides, oxides, oxide hydrates, borates, phosphates, phosphites, silicates and the like, e.g. aluminum hydrogen phosphite, melem or a melamine metal phosphate, e.g., a melamine metal phosphate wherein the metal comprises aluminum, magnesium or zinc. In particular embodiments the one or more additional flame retardant, synergist or flame retardant adjuvant comprises an aluminum tris(dialkylphosphinate), aluminum hydrogen phosphite, methylene-diphenylphosphine oxide-substituted polyaryl ether, xylylenebis(diphenylphosphine oxide), 4,4'-bis(diphenylphosphinylmethyl)-1,1'-biphenyl, ethylene bis-1,2-bis-(9,10-dihydro-9-oxy-10-phosphaphenanthrene-10-oxide)ethane, melem, or dimelamine zinc pyrophosphate.

One particular embodiment is to a synergistic mixture comprising the flame retardant of the invention and aluminum tris(diethylphosphinate).

For example, the flame retardant of the invention may be combined with an additional flame retardant, synergist or adjuvant in a range of 100:1 to 1:100 by weight of inventive flame retardant to the total weight of additional flame retardant, synergist and adjuvant. Depending on the additional flame retardant, synergist or adjuvant, excellent can be obtained using a range of 10:1 to 1:10 by weight of flame retardant to additional flame retardant, synergist and/or adjuvant, for example, weight ratios ranging from 7:1 to 1:7, 6:1 to 1:6, 4:1 to 1:4, 3:1 to 1:3 and 2:1 to 1:2 are used to good benefit. The inventive flame retardant is typically the majority component in such a combination, e.g., a 10:1 to 1.2:1 ratio or a 7:1 to 2:1 ratio by weight of the inventive flame retardant material to additional flame retardant, synergist and/or adjuvant, but the inventive material can also be the minor component of the mixture, e.g., a 1:10 to 1:1.2 ratio or a 1:7 to 1:2 ratio of flame retardant to additional flame retardant, synergist and/or adjuvant synergist.

The flame retardant polymer composition of the invention will also typically contain one or more of the common stabilizers or other additives frequently encountered in the art such as phenolic antioxidants, hindered amine light stabilizers (HALS), the ultraviolet light absorbers, phosphites, phosphonites, alkaline metal salts of fatty acids, hydrotalcites, metal oxides, borates, epoxidized soybean oils, the hydroxylamines, the tertiary amine oxides, lactones, thermal reaction products of tertiary amine oxides, thiosynergists, basic co-stabilizers, for example, melamine, melem etc., polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate, nucleating agents, clarifying agents, etc.

Other additives may also be present, for example, plasticizers, lubricants, emulsifiers, pigments, dyes, optical brighteners, other flameproofing agents, anti-static agents, blowing agents, anti drip agents, e.g., PTFE, and the like.

Optionally the polymer may include fillers and reinforcing agents, for example, calcium carbonate, silicates, glass fibers, talc, kaolin, mica, barium sulfate, metal oxides and hydroxides, carbon black and graphite. Such fillers and reinforcing agents may often be present at relatively high concentrations, including formulations where the filler or reinforcement is present in concentrations of over 50 wt % based on the weight of the final composition. More typically, fillers and reinforcing agents are present from about 5 to about 50 wt %, e.g., about 10 to about 40 wt % or about 15 to about 30 wt % based on the weight of the total polymer composition.

EXAMPLES

Comparative Example 1

To a solution of 96.0 g methylphosphonic acid (1.00 mol) in 210 mL deionized water is slowly added 54.1 g aluminum ethoxide (0.334 mol) under nitrogen. The reaction mixture is then stirred at room temperature for 16 h. The solution is subsequently concentrated and dried at 100° C. in vacuo to afford a clear, colorless solid. Thermal analysis, as shown in FIG. 1, indicated the loss of one mole of water starting at approximately 250° C. Elemental analysis: 29.8% P, 9.0% Al; calc'd 29.8% P, 8.7% Al.

20 parts of the salt and 30 parts glass were compounded into 50 parts polyamide 66 using a Haake Rheocord 90 equipped with a three piece Brabender measuring head. A decrease in torque was observed during compounding, which could signify polymer degradation, resulting in a material resembling wet newspaper that was friable upon cooling and dusty after grinding. Analysis of the compounded material, which could not be molded, by gel permeation chromatography (GPC) and differential scanning calorimetry (DSC) provided additional evidence of degradation.

Example 1—Flame Retardant from Methylphosphonic Acid Aluminum Salt, FR-INV1

Figure 2:
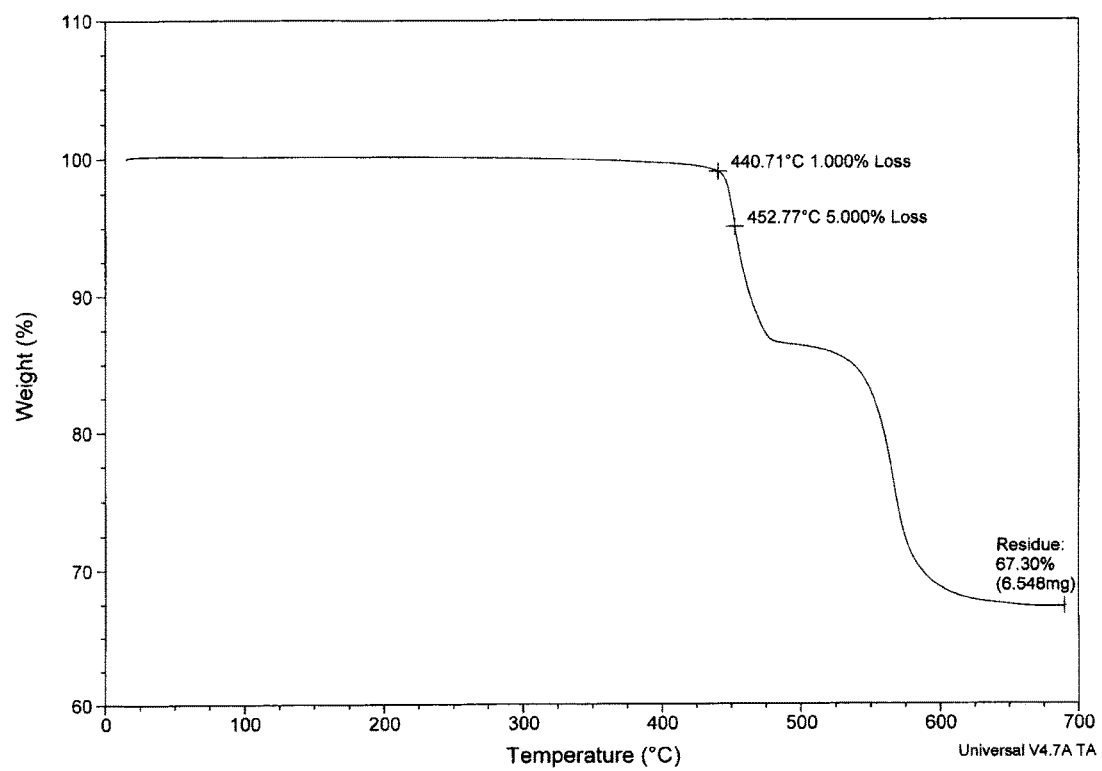
FIG. 2 displays the thermal analysis data of the flame retardant material of Example 1.

To a cooled solution of 48.0 g methylphosphonic acid (500 mmol) in 210 ml deionized water is slowly added 27.0 g aluminum ethoxide (167 mmol) under nitrogen. The reaction is then allowed to warm to room temperature and is stirred for 16 h. The solution is subsequently concentrated and dried at 100° C. in vacuo to afford a clear, colorless solid. Thermal analysis as indicated the loss of one mole of water starting at 250° C. The colorless solid was heated for 4 h at 280° C. resulting in an off-white solid that is stable to >400° C., as shown in FIG. 2. Elemental analysis: 31.5% P, 9.0% Al.

Comparative Example 2

To a stirred solution of 37.9 g ethylphosphonic acid (344 mmol) in 150 mL deionized water is added a solution of 27.7 g aluminum chloride hexahydrate (115 mmol) in 150 mL deionized water. The solution is then concentrated in vacuo to remove water and HCl. Drying at 130° C. in a vacuum oven affords a white powder. Thermal analysis indicated the loss of one mole of water starting at approximately 200° C. Elemental analysis: 25.0% P, 6.9% Al.

20 parts of the salt and 30 parts glass were compounded into 50 parts polyamide 66 using a Haake Rheocord 90. Low torque was observed throughout compounding, which could signify polymer degradation, with the formulation swelling out of the bowl towards the end of the run resulting in a material that foamed due to escaped gases and that was friable upon cooling and dusty after grinding. Analysis of the compounded material, which could not be molded, by GPC and DSC provided additional evidence of degradation.

Example 2—Flame Retardant from Ethylphosphonic Acid Aluminum Salt, FR-INV2

To a stirred solution of 149.5 g ethylphosphonic acid (1.36 mol) in 500 mL deionized water is added a solution of 109.3 g aluminum chloride hexahydrate (0.453 mol) in 250 mL deionized water. The solution is then concentrated and dried at 130° C. in vacuo to remove water and HCl. Thermal analysis indicated the loss of one mole of water starting at 180° C. Heating the dried salt for 3 h at 225° C. affords a white powder that is stable to approximately 400° C. Elemental analysis: 27.3% P, 7.6% Al.

Example 3—Flame Retardant from Ethylphosphonic Acid Calcium Salt, FR-INV3

To a stirred solution of 52.1 g ethylphosphonic acid (473 mmol) in 250 mL deionized water is slowly added 17.5 g calcium hydroxide (236 mmol). The solution is then concentrated and dried at 100° C. in vacuo. Thermal analysis indicated the loss of one mole of water staring at 220° C. Heating the dried salt for 3 h at 290° C. affords a white powder that is stable >400° C. Elemental analysis: 25.3% P, 16.3% Ca.

Formulations comprising flame retardants from Examples 1, 2 and 3 and various synergists were compounded into polyamide 66 with glass using a Haake Rheocord 90 and molded with a BabyPlast Mini-Molder into 1/16" bars which were subjected to standard UL 94 Vertical Burn Test. Formulations and results are listed in Table 1 below.

TABLE 1

| | FR Data | | | | | | | | | | | |
|---|---|---|---|---|---|---|---|---|---|---|---|---|
| Formulation | 1 | 2 | 3 | 4 | 5 | 6 | 7 | 8 | 9 | 10 | 11 | 12 |
| Nylon 66 | 56.3 | 45 | 53.8 | 57.5 | 50.7 | 53 | 50.3 | 51.7 | 46.3 | 53.8 | 54.4 | 45 |
| Glass | 30 | 30 | 30 | 30 | 30 | 30 | 30 | 30 | 30 | 30 | 30 | 30 |
| FR-INV1 | 13.7 | 25 | 13.7 | 10 | 13.7 | 13.7 | 13.7 | 13.7 | 13.7 | 13.7 | | |
| FR-INV2 | | | | | | | | | | | 15.6 | |
| FR-INV3 | | | | | | | | | | | | 15 |
| SYN1 | | | 2.5 | 2.5 | | | | | | | | |
| SYN2 | | | | | 5.6 | | | | | | | |
| SYN3 | | | | | | 3.3 | | | | | | |
| SYN4 | | | | | | | 6 | | | | | |
| SYN5 | | | | | | | | 4.6 | | | | |
| SYN6 | | | | | | | | | 10 | | | |
| SYN7 | | | | | | | | | | 2.5 | | |
| SYN8 | | | | | | | | | | | | 10 |
| UL 94 | V-1 | V-0 | V-0 | V-1 | V-0 | V-0 | V-0 | V-0 | V-0 | V-1 | V-0 | V-0 |

Synergists used in the FR formulations:
SYN1: Aluminum tris(diethylphosphinate), Exolit® OP 1230

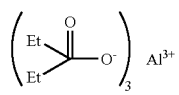

TABLE 1-continued

FR Data

| Formulation | 1 | 2 | 3 | 4 | 5 | 6 | 7 | 8 | 9 | 10 | 11 | 12 |
|---|---|---|---|---|---|---|---|---|---|---|---|---|

SYN2: Methylene-diphenylphosphine oxide-substituted polyaryl ether

SYN3: p-Xylylenebis(diphenylphosphine oxide)

SYN4: 4,4'-bis(diphenylphosphinylmethyl)-1,1'-biphenyl

SYN5: 1,2-bis-(9,10-dihydro-9-oxy-10-phosphaphenanthrene-10-oxide)ethane

SYN6: Melem, Delacal ® NFR HP

SYN7: Aluminum hydrogen phosphite
$Al_2(HPO_3)_3$

SYN8: Dimelamine zinc pyrophosphate, Safire ® 400

What is claimed:

1. A moldable thermoplastic flame retardant polymer composition comprising:
   a) a thermoplastic polymer, into which thermoplastic polymer has been compounded by melt processing without negatively impacting the physical, thermoplastic properties of the thermoplastic polymer,
   b) from 1% to 50%, by weight based on the total weight of the flame retardant polymer composition, of a flame retardant material, wherein said flame retardant material is a product of thermal conversion, before compounding into the thermoplastic polymer, of one or more compounds of formula (I) into a different chemical species having greater thermal stability than the one or more compounds of formula (I) as determined by differential scanning calorimetry or weight loss data obtained while increasing temperatures during thermal analysis, which product is obtained by a process comprising heating in the absence of other components at temperatures of higher than 200° C. from about 0.01 hour to about 20 hours one or more than one compound of formula (I)

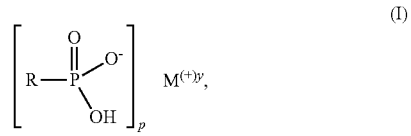

(I)

wherein
R is $C_{1-12}$ alkyl, $C_{6-10}$ aryl, $C_{7-18}$ alkylaryl, or $C_{7-18}$ arylalkyl, wherein said alkyl, aryl, alkylaryl, or arylalkyl are unsubstituted or are substituted by halogen, hydroxyl, amino, $C_{1-4}$ alkylamino, di-$C_{1-4}$ alkylamino, $C_{1-4}$ alkoxy, carboxy or $C_{2-5}$ alkoxycarbonyl;

M is a metal, y is a number of from 1 to 4 so that $M^{(+)y}$ is a metal cation where (+)y represents the charge formally assigned to the cation, and p is a number of from 1 to 4 to form the flame retardant material.

2. The moldable thermoplastic flame retardant polymer composition according to claim 1 wherein M in formula (I) is Li, K, Na, Mg, Ca, Ba, Zn, Zr, B, Al, Si, Ti, Sn or Sb.

3. The moldable thermoplastic flame retardant polymer composition according to claim 1 wherein M in formula (I) is Al or Ca.

4. The moldable thermoplastic flame retardant polymer composition according to claim 1 wherein in formula (I) R is unsubstituted $C_{1-6}$ alkyl, $C_6$ aryl, $C_{7-10}$ alkylaryl, or $C_{7-12}$ arylalkyl.

5. The moldable thermoplastic flame retardant polymer composition according to claim 4 wherein R is methyl, ethyl, propyl, or isopropyl.

6. The moldable thermoplastic flame retardant polymer composition according to claim 5 wherein M in formula (I) is Al or Ca.

7. The moldable thermoplastic flame retardant polymer composition according to claim 6 wherein the thermoplastic polymer comprises one or more of a polyolefin homopolymer, polyolefin copolymer, rubber, polyester, polyurethane, polysulfone, polyimide, polyphenylene ether, styrenic polymer, styrenic copolymer, polycarbonate, acrylic polymer, polyamide, polyacetal, or a blend thereof.

8. The moldable thermoplastic flame retardant polymer composition according to claim 7 wherein the thermoplastic polymer comprises one or more of a styrenic polymer, polyolefin, polyester, polycarbonate, polyamide, or polyurethane.

9. The moldable thermoplastic flame retardant polymer composition according to claim 8 wherein the thermoplastic polymer comprises a polyalkylene terephthalate, HIPS, or polyamide, which thermoplastic polymer optionally further comprises a reinforcing agent.

10. The moldable thermoplastic flame retardant polymer composition according to claim 9 wherein the thermoplastic polymer comprises polybutylene terephthalate, polyethylene terephthalate, glass filled polybutylene terephthalate, glass filled polyethylene terephthalate, polyamide or a glass filled polyamide.

11. The moldable thermoplastic flame retardant polymer composition according to claim 10 wherein the polyamide or glass filled polyamide comprises nylon 46, nylon 4T, nylon 6T/66 copolymer, or nylon 9T.

12. The moldable thermoplastic flame retardant polymer composition according to claim 7 wherein the thermoplastic polymer further comprises a reinforcing agent.

13. The moldable thermoplastic flame retardant polymer composition according to claim 7 further comprising (c) one or more compounds selected from the group consisting of additional flame retardant, synergist and flame retardant adjuvant.

14. The moldable thermoplastic flame retardant polymer composition according to claim 13 wherein the one or more compounds selected from the group consisting of additional flame retardants, synergists and flame retardant adjuvants comprises an aluminum tris(dialkylphosphinate), aluminum hydrogen phosphite, a methylene-diphenylphosphine oxide-substituted polyaryl ether, a xylylenebis(diphenylphosphine oxide), 1,2-bis-(9,10-dihydro-9-oxy-10-phosphaphenanthrene-10-oxide)ethane, a 4,4'-bis(diphenylphosphinylmethyl)-1,1'-biphenyl, melem, or dimelamine zinc pyrophosphate.

15. The moldable thermoplastic flame retardant polymer composition according to claim 1 wherein the thermoplastic polymer comprises one or more of a polyolefin homopolymer, polyolefin copolymer, rubber, polyester, polyurethane, polysulfone, polyimide, polyphenylene ether, styrenic polymer, styrenic copolymer, polycarbonate, acrylic polymer, polyamide, polyacetal, or a blend thereof.

16. The moldable thermoplastic flame retardant polymer composition according to claim 15 wherein the thermoplastic polymer comprises one or more of a styrenic polymer, polyolefin, polyester, polycarbonate, polyamide, or polyurethane.

17. The moldable thermoplastic flame retardant polymer composition according to claim 16 wherein the thermoplastic polymer comprises a polyalkylene terephthalate, HIPS, or polyamide, and wherein the thermoplastic polymer optionally further comprises a reinforcing agent.

18. The moldable thermoplastic flame retardant polymer composition according to claim 17 wherein the thermoplastic polymer comprises polybutylene terephthalate, polyethylene terephthalate, glass filled polybutylene terephthalate, glass filled polyethylene terephthalate, a polyamide or a glass filled polyamide.

19. The moldable thermoplastic flame retardant polymer composition according to claim 18 wherein the polyamide or glass filled polyamide comprises nylon 46, nylon 4T, nylon 6T/66 copolymer, or nylon 9T.

20. The moldable thermoplastic flame retardant polymer composition according to claim 15 wherein the thermoplastic polymer further comprises a reinforcing agent.

21. The moldable thermoplastic flame retardant polymer composition according to claim 1 wherein the thermoplastic polymer comprises one or more of a polyphenylene ether/styrenic resin blend, ABS, polyvinyl chloride/ABS blend, methacrylonitrile containing ABS, α-methylstyrene containing ABS, polyester/ABS, polycarbonate/ABS, impact modified polyester or impact modified polystyrene.

22. The moldable thermoplastic flame retardant polymer composition according to claim 1 further comprising (c) one or more compounds selected from the group consisting of additional flame retardants, synergists and flame retardant adjuvants.

23. The moldable thermoplastic flame retardant polymer composition according to claim 22, wherein the one or more compounds selected from the group consisting of additional flame retardants, synergists and flame retardant adjuvants comprise halogenated flame retardants, alkyl or aryl phosphine oxide flame retardants, alkyl or aryl phosphate flame retardants, alkyl or aryl phosphonates, alkyl or aryl alkylphosphinates, or salts of alkyl or aryl phosphinic acid.

24. The moldable thermoplastic flame retardant polymer composition according to claim 23 wherein compounds selected from the group consisting of additional flame retardants, synergists and flame retardant adjuvants comprise an aluminum tris(dialkylphosphinate).

25. The moldable thermoplastic flame retardant polymer composition according to claim 22 wherein the one or more compounds selected from the group consisting of additional flame retardants, synergists and flame retardant adjuvants comprise melamine, melamine derivatives, melamine condensation products, melamine salts, phosphine oxides, polyphosphine oxides, or metal hydroxides, oxides, oxide hydrates, borates, phosphates, phosphites or silicates.

26. The moldable thermoplastic flame retardant composition according to claim 25 wherein the one or more compounds selected from the group consisting of additional flame retardants, synergists and flame retardant adjuvants comprise aluminum hydrogen phosphite, benzylic phosphine oxides, poly benzylic phosphine oxides, melem or melamine metal phosphate wherein the metal comprises aluminum, zinc or magnesium.

27. The moldable thermoplastic flame retardant polymer composition according to claim 22 comprising (c) one or more additional flame retardant, synergist or flame retardant adjuvant, wherein the one or more compounds selected from the group consisting of additional flame retardants, synergists and flame retardant adjuvants comprises an aluminum tris(dialkylphosphinate), aluminum hydrogen phosphite, methylene-diphenylphosphine oxide-substituted polyaryl ether, xylylenebis(diphenylphosphine oxide), 1,2-bis-(9,10-dihydro-9-oxy-10-phosphaphenanthrene-10-oxide)ethane, a 4,4'-bis(diphenylphosphinylmethyl)-1,1'-biphenyl, melem, or dimelamine zinc pyrophosphate.

28. A process for increasing the flame resistance of a thermoplastic polymer comprising heating in the absence of other components at temperatures of about 200° C. or higher one or more than one compound of formula (I)

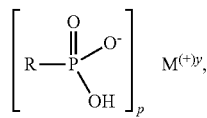

(I)

wherein R is $C_{1-12}$ alkyl, $C_{6-10}$ aryl, $C_{7-18}$ alkylaryl, or $C_{7-18}$ arylalkyl, wherein said alkyl, aryl, alkylaryl, or arylalkyl are unsubstituted or are substituted by halogen, hydroxyl, amino, $C_{1-4}$ alkylamino, di-$C_{1-4}$ alkylamino, $C_{1-4}$ alkoxy, carboxy or $C_{2-5}$ alkoxycarbonyl;

M is a metal, y is a number of from 1 to 4 so that $M^{(+)y}$ is a metal cation where (+)y represents the charge formally assigned to the cation, and p is a number of from 1 to 4;

to convert the one or more than one compound of formula (I) into a different chemical species having greater thermal stability than the one or more compound of formula (I) as determined by differential scanning calorimetry or weight loss data obtained while increasing temperatures during thermal analysis to prepare a flame retardant material followed by incorporating the flame retardant material into a thermoplastic polymer resin by melt processing of the polymer and flame retardant at elevated temperature without negatively impacting the physical properties of the thermoplastic polymer, optionally with one or more additional flame retardant, synergist or flame retardant adjuvant, to provide a moldable thermoplastic flame retardant polymer composition.

* * * * *